(12) United States Patent
Koop et al.

(10) Patent No.: US 7,098,344 B2
(45) Date of Patent: Aug. 29, 2006

(54) REACTION OF CARBONYL COMPOUNDS WITH ORGANOMETALLIC REAGENTS

(75) Inventors: Ulrich Koop, Rossdorf (DE); Holger Krummradt, Pfungstadt (DE); Michael Schwarz, Weiterstadt (DE); Joeran Stoldt, Weiterstadt (DE); Juergen Eckstein, Rossdorf (DE); Stefan Zehner, Schaafheim (DE); Wolfgang Melichar, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 10/169,310

(22) PCT Filed: Jan. 10, 2001

(86) PCT No.: PCT/EP01/00248

§ 371 (c)(1),
(2), (4) Date: Jul. 3, 2002

(87) PCT Pub. No.: WO01/51434

PCT Pub. Date: Jul. 19, 2001

(65) Prior Publication Data

US 2003/0004357 A1    Jan. 2, 2003

(30) Foreign Application Priority Data

Jan. 14, 2000    (DE) ................................ 100 01 317

(51) Int. Cl.
*C07D 513/04* (2006.01)

(52) U.S. Cl. .................................................. 548/303.7

(58) Field of Classification Search .............. 548/303.7
See application file for complete search history.

(56) References Cited

U.S. PATENT DOCUMENTS

| 3,740,416 | A | * | 6/1973 | Gerecke et al. .......... 548/303.7 |
| 5,358,670 | A |   | 10/1994 | Turnbull et al. |
| 5,708,185 | A | * | 1/1998 | Hirata et al. ............. 548/303.7 |
| 5,847,152 | A | * | 12/1998 | Eckstein et al. ......... 548/303.7 |
| 6,457,854 | B1 | * | 10/2002 | Koop et al. ................. 366/336 |

FOREIGN PATENT DOCUMENTS

| DE | 44 11 101 |   | 10/1995 |
| DE | 19746583 A1 | * | 4/1999 |
| JP | 07/188247 A2 | * | 7/1995 |
| WO | WO 99 22857 |   | 5/1999 |

OTHER PUBLICATIONS

Krummradt et al., Microreaction Technology Industrial Prospects, Proceedings of the International Conference on Microreaction Technology, 3rd, Frankfurt, Apr. 18-21, 1999, pp. 181-186.*
Streitwieser, Jr. and Heathcock, Introduction to Organic Chemistry, 3rd Edition, Macmillan Publishing Company, New York, (1985), pp. 386, 387, 434 and 435.*
CAPLUS Abstract No. 1965:82660, 1965.

* cited by examiner

*Primary Examiner*—Laura L. Stockton
(74) *Attorney, Agent, or Firm*—Millen, White, Zelano & Branigan, P.C.

(57) ABSTRACT

A novel process for carrying out reactions of carbonyl compounds with organometallic reagents, in particular with Grignard reagents, is described.

20 Claims, 4 Drawing Sheets

REACTION OF CARBONYL COMPOUNDS WITH ORGANOMETALLIC REAGENTS

Figure 1:
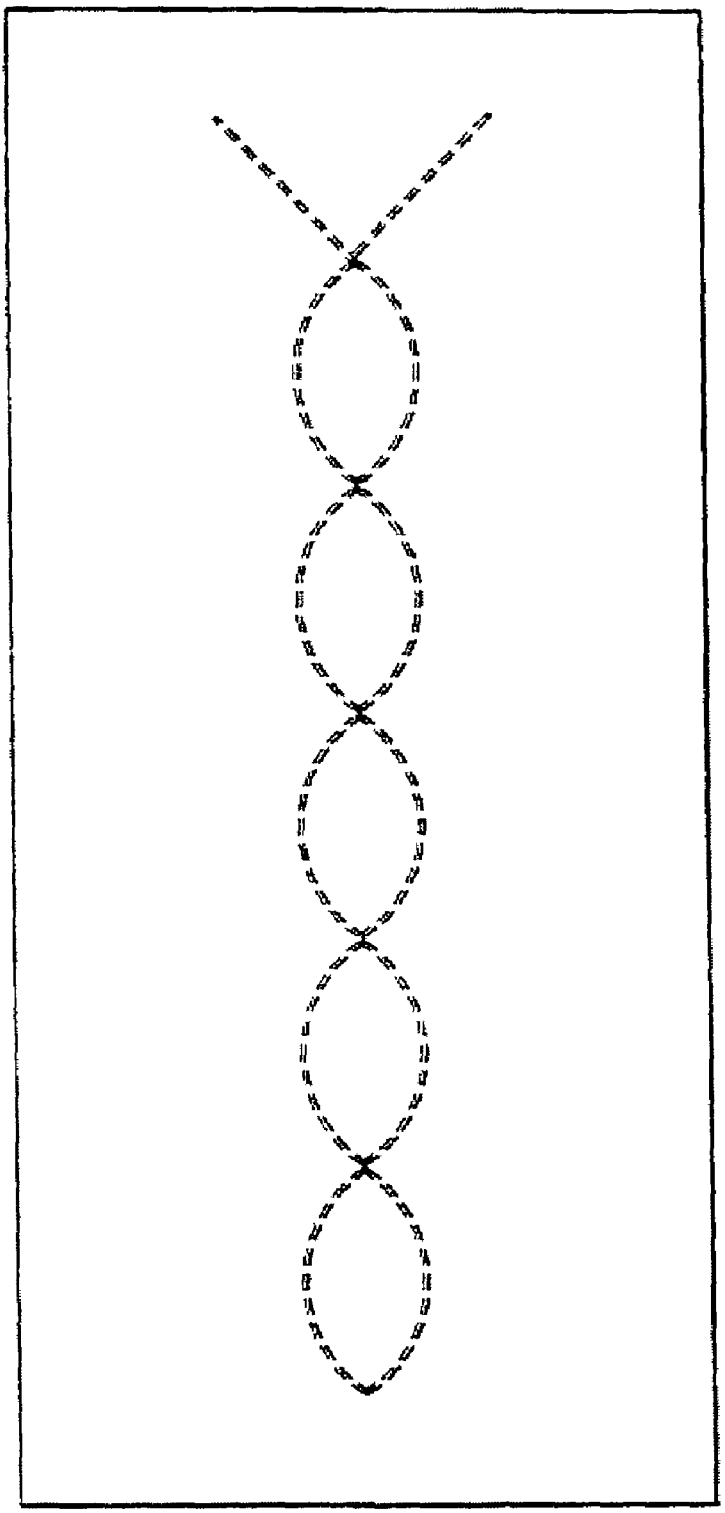

The invention relates to a novel process for carrying out reactions of carbonyl compounds with organometallic reagents, in particular with Grignard reagents.

The selectivity and quality of a chemical reaction are greatly affected by, inter alia, precise control of temperature and residence time. An example of this is a reaction which is described in the patent application DE 44 11 101 A1 ("Improved process for the preparation of a D-(+)-biotin intermediate"). This involves the following reaction:

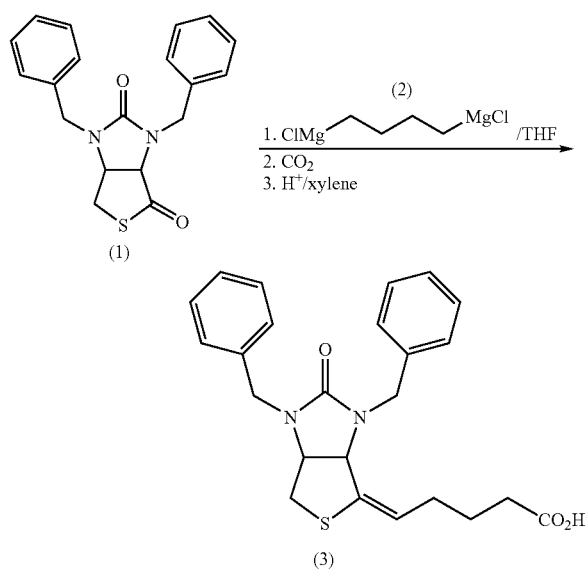

In order to carry out this reaction by this process, 1,4-(dichloromagnesium)-butane in tetrahydrofuran is initially introduced into a stirred apparatus. (+)-cis-1,3-Dibenzyl-hexahydro-1H-thieno[3,4d]imidazole-2,4-dione (1) dissolved in tetrahydrofuran is metered in at from −25 to −15° C. The intermediate formed by the reaction is subsequently reacted further with carbon dioxide. After exchange of the solvent (tetrahydrofuran is replaced by xylene), the mixture is dehydrated using 30% sulfuric acid at T>50° C. In order to remove the by-products formed, pH-controlled extractions are then carried out.

In spite of intensive optimisation attempts, the yield of this reaction on a production scale is currently about 65–75%. A disadvantage of carrying out the reaction in this way is the formation of various by-products in significant amounts, whose formation is greatly favoured by very long residence times ($\tau \approx 12$ hours).

The object of the present invention is therefore to provide a process by means of which reactions of carbonyl compounds with organometallic compounds can be carried out in a simple manner with improved selectivity and with a higher space-time yield.

This object is achieved by a process for carrying out reactions of carbonyl compounds with organometallic reagents which is characterised in that
a) the organometallic reagent is initially introduced in a solvent and heated to a particular temperature,
b) the carbonyl compound is initially introduced separately in a suitable solvent and heated to a particular temperature,
c) the solutions of a) and b) are, for reaction, pumped into a mini/micromixer held at a particular temperature, optionally passed through a downstream residence zone in the form of a very thin line, which may likewise be heated to a certain temperature, with a defined residence time being set,
d) the exiting reaction mixture is optionally subsequently reacted in a downstream reaction, and
e) the resultant product mixture is worked up.

The temperature-controlled mini/microreactor used in the process according to the invention is a plate-form micromixer, in which, if desired, the starting materials are combined in a 180° T-piece, and, if desired, intensive mixing is carried out in plait-shaped thin lines.

Organometallic reagents which can be employed in the process are both Grignard reagents and organolithium compounds. Accordingly, it is possible to employ compounds from the group consisting of 1,4-(dichloromagnesium)-butane, 3,4,5-trifluoro-1-bromomagnesiumbenzene and n-butyllithium.

The carbonyl compound employed can be a compound selected from the group consisting of aliphatic, cycloaliphatic and heterocyclic ketones.

The process according to the invention is particularly advantageous for the reaction of organometallic compounds with carbonyl compounds selected from the group consisting of 4-(pentyl-1-cyclohexyl)cyclohexan-4-one (4) and (+)-cis-1,3-dibenzylhexahydro-1H-thieno[3,4d]imidazole-2,4-dione.

Solvents which can be used for the organometallic compound, but also for the carbonyl compound are aprotic nucleophilic solvents. Suitable solvents are selected from the group consisting of tetrahydrofuran, diethyl ether, dioxane and dibutyl ether.

The process according to the invention can be carried out at a constant temperature between −40 and +120° C., preferably up to 60° C.

In a particular embodiment of the process, the reaction mixture leaving the mini/micromixer is conveyed into a storage tank or stirred reactor by means of a downstream pump.

Downstream reactions which can be carried out as part of the process according to the invention are reaction with carbon dioxide or hydrolysis.

Investigations have now shown that significantly higher yields are obtained in these reactions if the reaction of the starting materials is carried out with a residence time τ of <10 sec., with particular importance being attached to intensive mixing of the starting materials for the Grignard reaction. In the course of the investigations, it has been found that it is particularly advantageous if this first step is carried out continuously in a micro/mini reactor. The term "microreactor" is taken to mean a unit having flow channels having a size of from 1 to 1000 µm. By contrast, a "minireactor" has flow cross sections in the range >1000 µpm.

This enables the reaction to be carried out with intensive mixing and a defined residence time. At the same time, it is ensured under these conditions that the reaction mixture is kept constant at a defined temperature during the reaction in the reactor under virtually ideal conditions, namely at from −40 to, if desired, +120° C., depending on the starting materials employed.

In accordance with the invention, the preparation of the above-mentioned intermediate for the preparation of biotin is carried out with intensive mixing of the solutions of the Grignard reagent and thiolactone starting materials in a continuously operated mini/microreactor at a defined temperature. After having been passed, if desired, through a very thin, temperature-controlled downstream residence-time zone after leaving the microreactor, the resultant precursor is carboxylated using carbon dioxide in a suitable downstream reactor. The process parameters of pressure, temperature and mass flow rate are measured and regulated at various points.

The process described is generally suitable for the reaction of organometallic reagents with carbonyl compounds since the process parameters of concentration ratio, pressure, temperature and flow rate or residence time can be set precisely. With the possibility of precise reaction control and the use of small reactor volumes, a high safety level is achieved in this way.

The following procedure is employed for carrying out the above-mentioned reaction for the preparation of the intermediate of biotin: the thiolactone (1) dissolved in tetrahydrofuran is reacted continuously with the Grignard compound (2) in either a microreactor or a minireactor with downstream residence-time zone (residence time: $\tau<10$ s). The precursor obtained is passed directly into a stirred apparatus filled with gaseous carbon dioxide. The further work-up of the crude product corresponds to the batch process as also described in DE 44 11 101 A1. The analytical data (NMR, TLC) agree with those of the batch reaction.

In various experiments in which, as reaction parameter, the residence time in the microreactor was varied, high yields of the desired product were, surprisingly, achieved. For example, the following yields were obtained (flow rate 2 l/h per starting material, $C_{Grignard}:C_{thiolactone}=2:1$ to 1.5:1):
96.5% at –10° C.
90.1% at 40° C.
92% at 15° C.

These results were achieved even under conditions which have as yet not been optimised, so that further improvements can be expected.

For performance on a pilot-plant scale, static minimixers as described in DE 19746583 (FIG. 1) were employed. In this case, for example, the following yields were achieved:
94.0% at –25° C., 2 l/h per starting material
95.6% at –10° C., 2 l/h per starting material
93.7% at 5° C., 2 l/h per starting material However, even with a very simplified mixer, in which the starting materials are merely combined with the aid of thin lines having an internal diameter of 2 mm in a temperature-controlled T-piece and, if desired, passed through a subsequent residence zone in the form of a thin line of the same diameter (FIG. 2), significantly higher yields than hitherto possible are achieved:
92.6% at about 5–10° C., 5 l/h per starting material, T-piece with an internal diameter of 2 mm
88.2% at 28–33° C., 30 kg/h per starting material, T-piece with an internal diameter of 2 mm
84% at 5–24° C., 5–30 kg/h per starting material, T-piece with an internal diameter of 4 mm and downstream static mixer (a number of experimental parameters were tested in a single batch here).

Even if the starting materials are combined at an angle of between 30° and 150°, a significant increase in yield can be observed.

If the starting materials in a static mixer are combined not only in a T-piece, but the resultant reaction mixture is also passed through plait-shaped lines (FIG. 3), even further increases in yield can be achieved, as experiments have shown.

Figure 4:
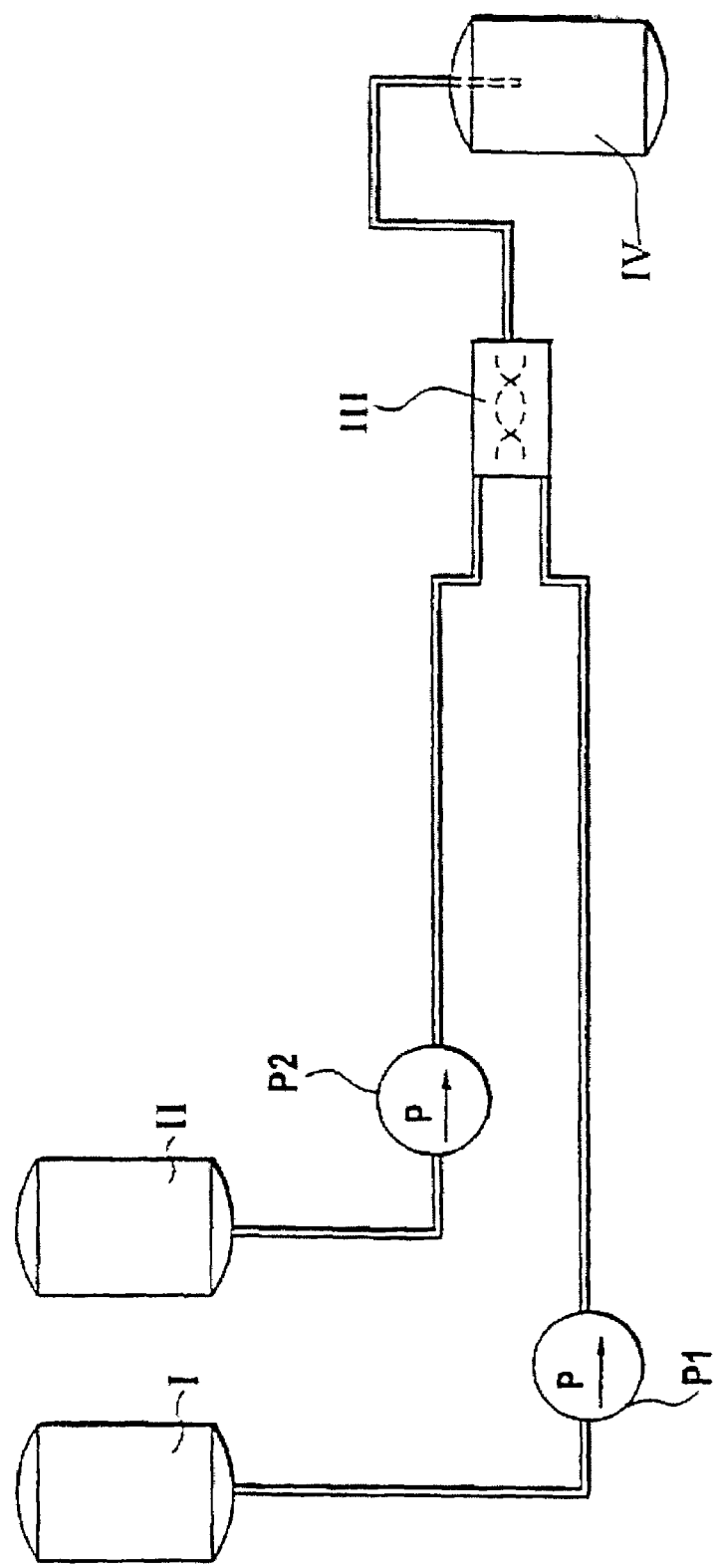

FIG. 4 shows a basic structure of a plant for the reaction of carbonyl compounds with organometallic reagents. The starting materials (1) and (2) are initially introduced into the two storage tanks or stirred tanks (I) and (II). Pressure and temperature sensors and flow meters are installed at various points in order to enable optimum control of the process. It is furthermore sensible for preheating zones to be integrated into the starting-material lines upstream of the reactor (III). It is furthermore possible to connect a plurality of reactors in series, which also enables multistep reactions to be carried out. For conveying the starting materials from the storage tanks (I) and (II) into the reactor (III), pumps are installed in between in the model plant in FIG. 4. After exiting from the static mini/microreactor, the reaction mixture is passed into a downstream storage tank or stirred tank (IV), in which a subsequent reaction, such as, for example, the reaction with $CO_2$, can take place.

Specifically, however, a suitable plant can also be constructed in such a way that a pump is installed downstream of the reactor in order to prevent undesired build-up of pressure.

In particular, pilot-plant scale experiments have been carried out with the following experimental set-up:

For the preparation of the Grignard compound, use was made of a standard stirred apparatus, which also served as stock vessel. The stock vessel used for the thiolactone solution was a flask with stirrer. The stock vessel used for the thiolactone solution was a flask with stirrer. A standard stirred apparatus served as collection vessel for the Grignard addition product and further reaction thereof with $CO_2$. For recording the temperature in the apparatus, a Pt100 temperature sensor was used. A steel tank was used as stock vessel for solvent (solvent≡S).

The starting-material solutions were conveyed into the mini/microreactors by means of suitable pumps through a filtration unit with control of the pressure and through non-return valves. The temperature of the thiolactone solution was controlled with the aid of a heat exchanger.

By means of three-way stopcocks, numerous ways of rinsing filters and lines were created, enabling the lines to be rinsed both with liquid and gaseous media as needed. For example, rinsing with inert gas or with solvent, or requisite pressure equalisation, is possible in this way.

The temperature-controllable minireactor consisted of a mixing unit and a reaction unit. The outlet from the reaction unit led into the above-mentioned stirred apparatus. A three-way stopcock located downstream of the reactor provided the means for sampling.

For control and recording of the reaction parameters, a suitable data acquisition and control unit was connected.

It is possible for the person skilled in the art to carry out the process in the manner described using an apparatus of appropriate construction whose individual parts are commercially available. The construction of the apparatus can be varied as needed to suit the particular reaction to be carried out.

Working examples are given below in order to illustrate the present invention.

EXPERIMENTAL PROCEDURE

1. Preparation of the Grignard Compound.

The 130 l stirred apparatus was repeatedly evacuated and aerated with nitrogen. 2.87 kg (116.9 mol) of magnesium turnings (99%) were initially introduced, and the apparatus was again rendered inert using nitrogen. 4.2 kg of THF were subsequently introduced on top of the turnings, the jacket temperature was set to 70° C., and 4.0 kg of a solution of 7.5 kg (59.1 mol) of 1,4-dichlorobutane (>99%) in 38.8 kg of THF were added. The reaction was initiated by addition of about 50 ml of 1,4-(dichloromagnesium)-butane. The jacket temperature was subsequently reduced to 60° C. When the starting amount had reacted, the remainder of the solution of 1,4-dichlorobutane in THF was added over the course of 2 hours 40 minutes at such a rate that the reaction mixture constantly refluxed (stirrer switched on after 10 minutes). The mixture was refluxed for a further 90 minutes (jacket temperature 80° C.) and then slowly cooled to 30° C. The solution was diluted with a further 55.9 kg of THF. The internal temperature was then kept constant at from 28 to 32° C. 110 kg of Grignard solution (c=0.5 mol/l) were obtained.

2. Preparation of the Thiolactone Solution.

11.2 kg (33.0 mol) of thiolactone (1) were dissolved in 89.8 kg of THF in a 200 l flask with stirrer. 101 kg of solution (c=0.30 mol/l) were obtained. The apparatus was kept under nitrogen.

3. Preparations and Performance of the Reaction in the Static Mixer.

All lines were firstly rinsed with anhydrous THF and dried and rendered inert using nitrogen. After 65 of THF had been introduced, the stirred apparatus was evacuated and aerated with carbon dioxide. The 800 l stirred apparatus, the mixing unit and the heat exchanger for the thiolactone precooling zone were cooled with brine (from about −14 to −12° C.).

Figure 5:
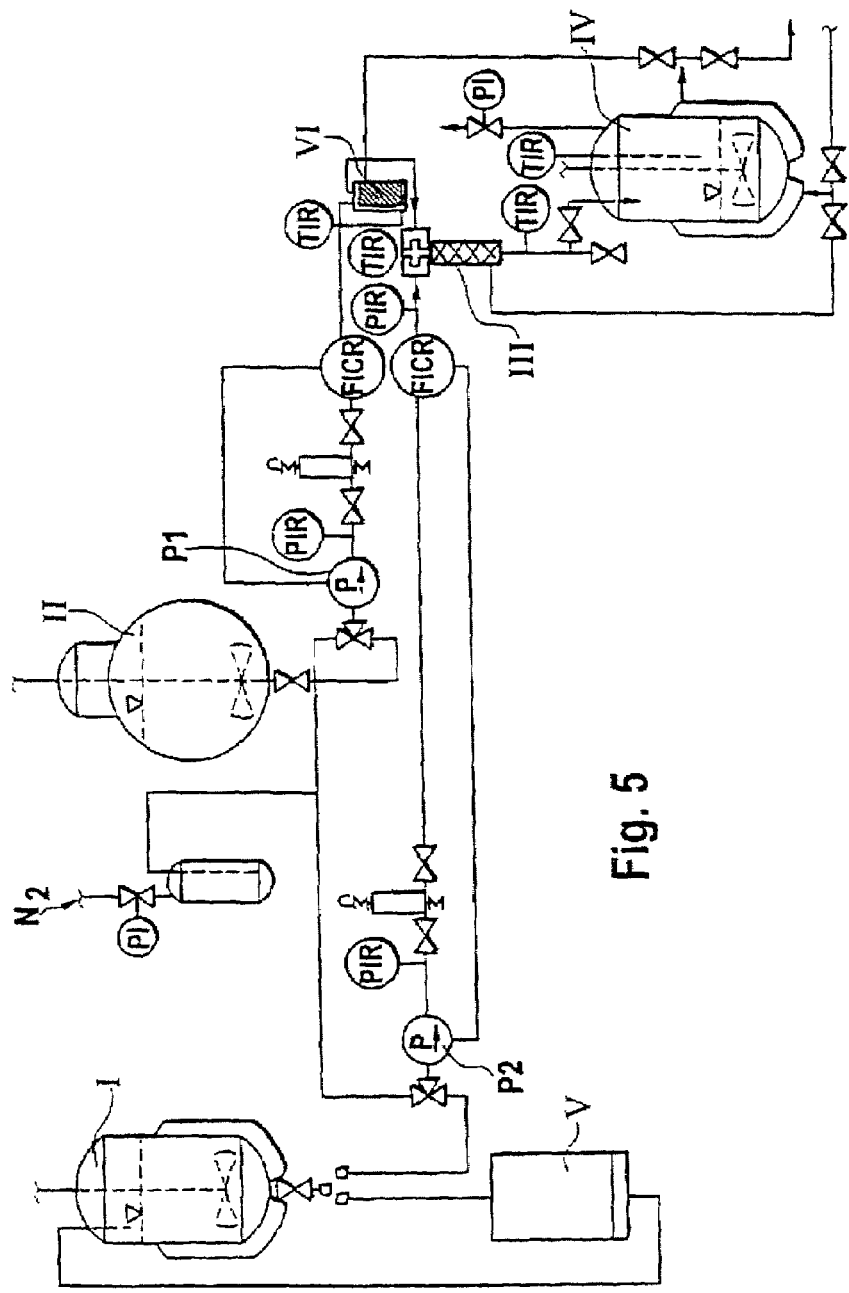

A flow chart of the plant used is shown in FIG. 5.

As described, the plant is constructed from the following components:

stirred apparatus with stirrer, 130 l, enamel, with temperature control stirred apparatus with stirrer, 800 l, enamel, with temperature control glass flask with stirrer, 200 l Seitz single-layer pressure filter, stainless steel, 120 l, Ø=65 cm 2 gear pumps, stainless steel, Gather Industries Pall cartridge filter, stainless-steel mesh, 50 pm, 2.5 l volume stainless-steel drum, pressure-resistant, 100 l heat exchanger made from 6 mm steel tubing, coil with length of 3 m 6 mm and 100 mm steel tubes Swadgelok connectors, stopcocks and hoses For the measurement and control system, the following sensors were employed in addition to the standard sensors of the 800 l stirred apparatus:

For temperature measurement downstream of the entire mixing unit temperature measurement of the brine downstream of the mixing unit and upstream of the precooler for thiolactone, =>Pt100 sensors, 6 mm steel casing, Cowie AG (Switzerland)

=>Pt100 sensors, 6 mm Teflon casing, Cowie AG (Switzerland)

were employed and for the pressure measurements

2× pressure measurement downstream of the gear pump upstream of the filter pressure measurement upstream of the mixer in the Grignard line, =>P41 pressure measurement transducer [steel membrane, M20×1.5, 0–10 bar absolute pressure, PMH (Prozeβ-und Maschinen-Automation GmbH (Philips, D)]

was employed.

Flow rates were measured using.

2× Coriolis mass flow meters

=>Massflo® Mass 3000/2100 Ex (measurement transducer and recorder), Danfoss Antriebs- und Regeltechnik GmbH The Grignard flow rate was set to 30 kg/h (3 kg were pumped into the 800 l stirred apparatus without reaction with thiolactone), and the thiolactone flow rate was adjusted with the aid of a factor (density difference). This operational setting (30 kg/h) was retained until all the Grignard solution had been consumed. The $CO_2$ flow rate had to be set to about 25 l/h.

After the consumption of 99.6 kg (≡32.5 mol of thiolactone) of thiolactone solution and about 110 kg of Grignard solution, the cooling was switched off, and $CO_2$ was subsequently passed through the apparatus for a further 30 minutes. The resultant suspension was stirred overnight.

The mixture was warmed to about 42° C. with vigorous stirring and evacuated to 400 mbar. THF was distilled off until the residue was very viscous. 30 l of xylene were added, and further THF was removed. After the addition of a further 30 l of xylene, 66 kg of 30% $H_2SO_4$ were slowly added with stirring, during which the mixture warmed to T=67° C. The mixture was stirred at maximum stirrer speed for a further 120 minutes at an internal temperature of 62–70° C., and the jacket temperature was subsequently reduced to 50° C. When the desired temperature had been reached, the stirrer was switched off. The aqueous phase was separated off at about 65° C., and the organic phase was cooled to 30° C. Through addition of about 45 l of 1 N NaOH, the pH was set to pH=9.37 with vigorous stirring. The stirrer was switched off, and the phases were separated after 1 hour (xylene 1). The aqueous phase was returned into the apparatus, and 60 l of xylene were added. The pH was set to pH=6.81 using about 4 l of 25% hydrochloric acid, the phases were separated (about 30 minutes), and the product in xylene was obtained (xylene 2).

Part-amounts of the two xylene phases were freed from solvent and water by azeotropic vacuum distillation. The total yields were determined from the masses obtained.

Xylene 1: 2.07 kg (by-products)

Xylene 2: 12.14 kg (main product, yield 88.2%)

During performance of this experiment, the temperature at the mixer outlet was 31–33° C. for about 2 hours and about 28–29° C. for the remainder of the time. A pressure increase of about 1 bar in the system as a whole was observed. The temperature of the Grignard solution was set to 30° C. The control behaviour of the Grignard pump rose by about 10 units. The maximum pressure in the system was about 4.5 bar at the end of the experiment.

Analysis of the by-products showed that they are a corresponding diolefin, the butylidene compound and the product of the reduction of the desired compound (3) as well as ureidthiol.

In the same way, 4-[4-(trans4-pentylcyclohexyl)-1-cyclohexen-1-yl]-1-tri-fluoromethoxybenzene (CCP-5-OCF3-enyl) (5) can be prepared using n-butyllithium. The starting materials employed were 4-bromotrifluoro-methoxybenzene (3) and 4-(4-pentylcyclohexyl)cyclohexan-4-one (4). After subsequent hydrolysis, the desired product (5) is obtained.

Furthermore, cyclohexylcyclohexan-3-one can be reacted with 3,4,5-trifluoro-1-bromomagnesiumbenzene at temperatures of between 0 and 60° C. Here too, the residence time can be shortened from a number of hours to less than 10 seconds. In contrast to the reaction described above, the yield and thus the product quality can be optimised by increasing the pressure and temperature, but it should be noted that the Grignard compound tends toward decomposition at above 100° C. in a highly exothermic reaction, and the boiling point of THF is 65° C. However, due to the inherent safety of the micromixer, this process can nevertheless be carried out at higher temperatures, so that the present invention enables the reaction to be carried out in a manner which is otherwise impossible

FIGURES

Figure 2:
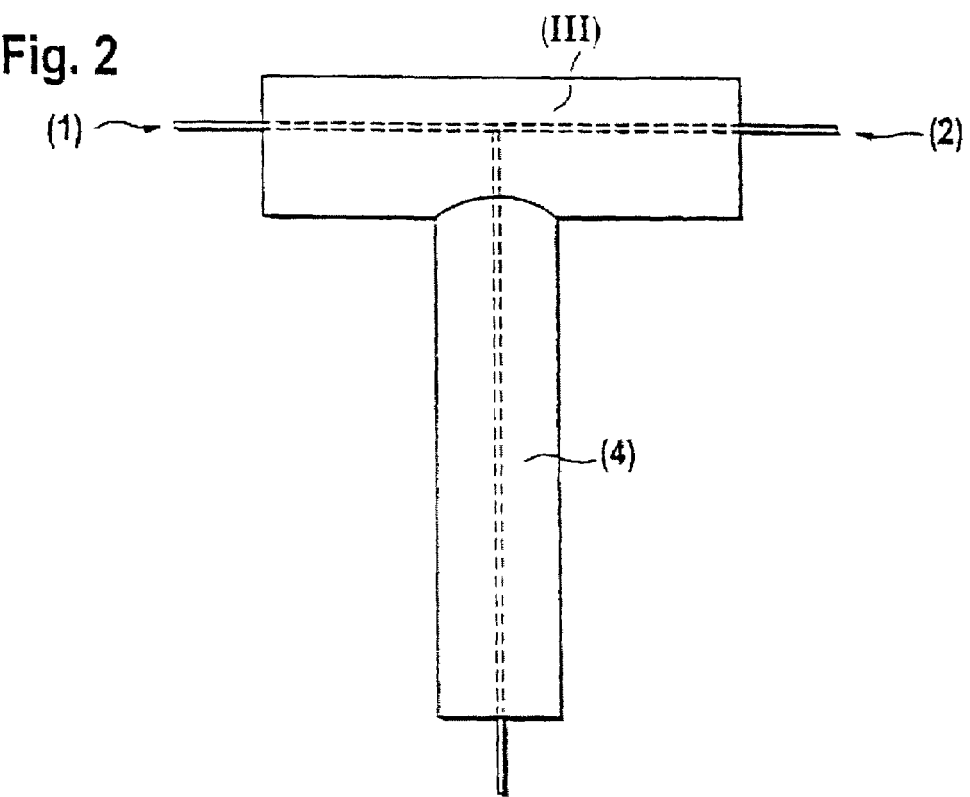
Figure 3:
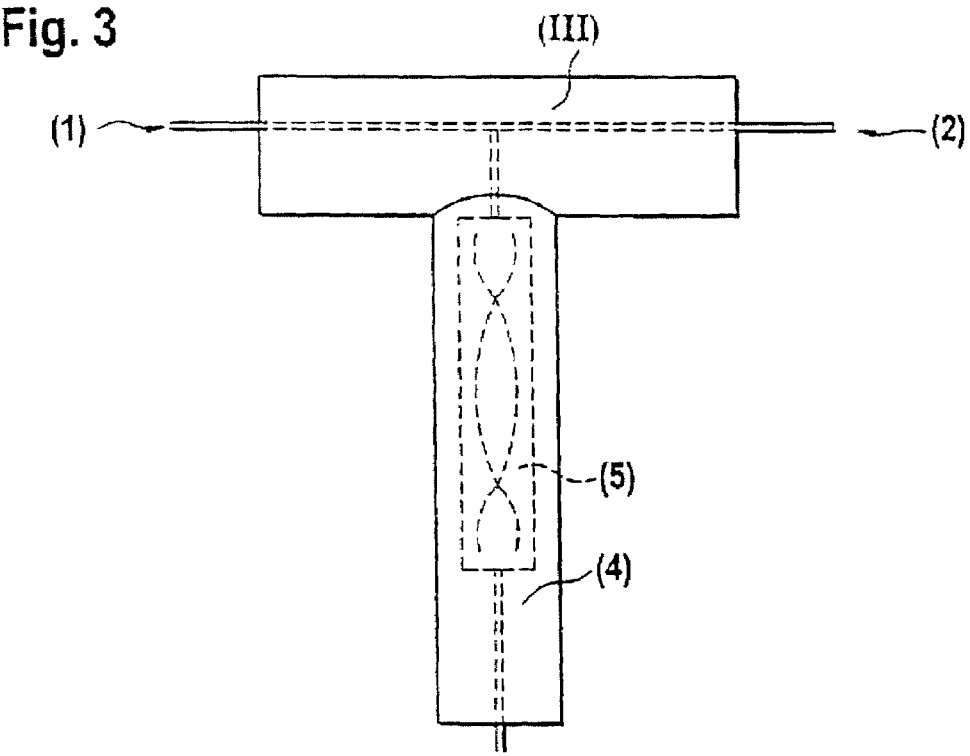

FIG. 1
Mini static mixer as already described in DE 19746583 A1
FIG. 2
T-piece mixer 1
Simplified mixer in which the starting materials (1) and (2) are combined in a temperature-controlled T-piece (III) with the aid of thin lines having an internal diameter of 2 mm which are surrounded by a cooling jacket (4). The internal diameter of the lines is 2 mm inside and 4 mm outside the cooling jacket.
FIG. 3
T-piece mixer 2
Static mixer as in FIG. 2 having an internal diameter of the lines in the T-piece (III) of 4 mm, but in which, after the starting materials (1) and (2) have been combined, the reaction mixture is passed through a static mixer having plait-shaped lines (5) having an internal diameter of about 4 mm.
FIG. 4
Basic structure of a plant:
Components of the plant are:
storage tanks or stirred tanks (I) and (II) containing starting materials 1 and 2 reactor (III)
storage tank or stirred tank (IV) for the reaction mixture pumps P1 and P2
FIG. 5
Structure of the plant used for the experiments:
stirred apparatus with stirrer, enamel, with temperature control (I)
stirred apparatus with stirrer, enamel, with temperature control (IV)
glass flask with stirrer (II)
Seitz single-layer pressure filter, stainless steel (V)
2 gear pumps (P1, P2)
heat exchanger (VI)
Pall cartridge filter; stainless steel drum, pressure resistant; 6 mm and 100 mm steel tubes; Swadgelok connectors, stopcocks and hoses.

The invention claimed is:

1. A process for carrying out a reaction of a carbonyl compound with an organometallic reagent to obtain an addition reaction product thereof, which comprises:
    a) providing the organometallic reagent in a solvent, heated to a particular temperature and filtered,
    b) providing the carbonyl compound separately in a solvent and heated to a particular temperature, and
    c) reacting the solutions of a) and b) by pumping into a mini/micromixer held at a certain temperature, such that the solutions intensively mix and react, to obtain a resultant reaction mixture containing the addition reaction product, optionally passing the resultant reaction mixture through a downstream residence zone in the form of a very thin line, which is optionally heated to a particular temperature, with a defined residence time being set.

2. Process according to claim 1, wherein the temperature controlled mini/microreactor used is a plate-form micromixer.

3. Process according to claim 1, wherein the organometallic reagent employed is a Grignard reagent or an organolithium compound.

4. Process according to claim 1, wherein the organometallic reagent used is a compound selected from the group consisting of 1,4-dichloromagnesiumbutane, 3,4,5-trifluoro-1-bromomagnesium-benzene and n-butyllithium.

5. Process according to claim 1, wherein the carbonyl compound employed is a compound selected from the group consisting of aliphatic, cycloaliphatic and heterocyclic ketones.

6. Process according to claim 1, wherein the carbonyl compound used is a compound selected from the group consisting of 4-(4-pentylcyclohexyl)cyclohexan-4-one (4) and (+)-cis-1,3-dibenzyl-hexahydro-1H-thieno[3,4d]imidazole-2,4-dione.

7. Process according to claim 1, wherein the solvent for a) and b) is an aprotic nucleophilic solvent.

8. Process according to claim 7, wherein the solvent for a) and b) is a solvent selected from the group consisting of tetrahydrofuran, diethyl ether, dioxane and dibutyl ether.

9. Process according to claim 1, wherein the reaction is carried out at a constant temperature between −40 and +120° C.

10. Process according to claim 1, wherein the reaction mixture leaving the mini/micromixer is conveyed into a storage tank or stirred reactor by means of a downstream pump.

11. Process according to claim 1, wherein a downstream reaction with carbon dioxide or a hydrolysis is carried out.

12. The process of claim 1, wherein intensive mixing is enhanced by including a static mixer with plait-shaped thin lines.

13. Process according to claim 1, wherein the reaction is carried out at a constant temperature of up to 60° C.

14. The process of claim 1, wherein the residence time in the mini/micromixer is <10 seconds.

15. A process for carrying out a reaction of a carbonyl compound with an organometallic reagent to obtain an addition reaction product thereof, which comprises:
    a) providing the organometallic reagent in a solvent, heated to a particular temperature and filtered,
    b) providing the carbonyl compound separately in a solvent and heated to a particular temperature, and
    c) reacting the solutions of a) and b) by pumping into a mini/micromixer held at a certain temperature, where the mini/micromixer combines the solutions of a) and b) in opposing streams by a 180° T-piece, such that the solutions intensively mix and react, to obtain a resultant reaction mixture containing the addition reaction product, optionally passing the resultant reaction mixture through a downstream residence zone in the form of a very thin line, which is optionally heated to a particular temperature, with a defined residence time being set.

16. The process of claim 15, wherein intensive mixing is enhanced by including, downstream of the joint of the T-piece, a static mixer with plait-shaped thin lines.

17. Process according to claim 15, wherein the organometallic reagent employed is a Grignard reagent or an organolithium compound.

18. Process according to claim 15, wherein the carbonyl compound employed is a compound selected from the group consisting of aliphatic, cycloaliphatic and heterocyclic ketones.

19. Process according to claim 15, wherein the reaction is carried out at a constant temperature between −40 and +120° C.

20. The process of claim 15, wherein the residence time in the mini/micromixer is <10 seconds.

* * * * *